(12) United States Patent
Wong

(10) Patent No.: US 8,178,832 B1
(45) Date of Patent: May 15, 2012

(54) RE-CALIBRATION METHODOLOGY FOR NDIR GAS SENSORS

(76) Inventor: Jacob Y. Wong, Goleta, CA (US)

( * ) Notice: Subject to any disclaimer, the term of this patent is extended or adjusted under 35 U.S.C. 154(b) by 0 days.

(21) Appl. No.: 13/149,738

(22) Filed: May 31, 2011

(51) Int. Cl.
G12B 15/00 (2006.01)
G01J 5/00 (2006.01)

(52) U.S. Cl. .................... 250/252.1; 250/343; 73/31.01; 702/85; 422/83

(58) Field of Classification Search .............. 78/31.02, 78/21.2, 23.21, 23.22; 250/338.5, 343, 344, 250/252.1; 356/437; 702/85; 422/83
See application file for complete search history.

(56) References Cited

U.S. PATENT DOCUMENTS

| | | | | |
|---|---|---|---|---|
| 4,578,762 A * | 3/1986 | Wong | ............................. | 702/32 |
| 5,163,332 A * | 11/1992 | Wong | ......................... | 73/863.23 |
| 5,222,389 A * | 6/1993 | Wong | ........................... | 73/31.02 |
| 5,340,986 A * | 8/1994 | Wong | ........................... | 250/343 |
| 5,341,214 A * | 8/1994 | Wong | ............................. | 356/437 |
| 5,347,474 A * | 9/1994 | Wong | ............................. | 702/86 |
| 5,502,308 A * | 3/1996 | Wong | ......................... | 250/338.5 |
| 6,061,141 A * | 5/2000 | Goldenberg et al. | ......... | 356/437 |
| 6,526,801 B2* | 3/2003 | Kouznetsov et al. | .......... | 73/1.03 |
| 7,180,595 B2* | 2/2007 | Willing et al. | ................ | 356/437 |

OTHER PUBLICATIONS

Yokogawa, General Specifications: IR200 NDIR Type Infrared Gas Analyzer, published Jun. 2006; Retrieved from the internet [Nov. 21, 2011], Retrieved from URL <http://www.yokogawa.com/an/download/general/GS11G02M01-01E.pdf>.*

* cited by examiner

*Primary Examiner* — David Porta
*Assistant Examiner* — Yara Green
(74) *Attorney, Agent, or Firm* — Roy L Anderson; Wagner, Anderson & Bright, PC

(57) ABSTRACT

A re-calibration method for a dual-beam NDIR gas sensor uses a calibration curve based upon a combination of physics and sensor measurement components of the sensor to calculate sample gas concentration, then determines a second gas concentration measurement by a secondary gas standard which is used with a reversed calibration curve algorithm to adjust the sensor measurement component. The calibration curve is based upon a gamma ratio ("G") that has been normalized by G when no sample gas is present in the sample chamber ("$G_0$"), G being a ratio of a signal channel output ("$V_S$") of the sensor divided by a reference channel output ("$V_R$") of the sensor. The concentration ("P") of sample gas in the sensor is calculated through use of the calibration curve by a gas detection equation of $P=F(x)=F(y/G_0)$, where x is a normalized ratio of $V_S/V_R$ and y is G. The reversed calibration curve algorithm is $P=F(x)=F(y/G_{ON})$, where $G_{ON}=y_1/x_2$, $y_1=G$ for the sensor, $x_2=F^{-1}$ ($P_2$) and $P_2$ is the second gas concentration of the sample gas.

25 Claims, 6 Drawing Sheets

RE-CALIBRATION METHODOLOGY FOR NDIR GAS SENSORS

FIELD OF THE INVENTION

The present invention is in the field of measuring instruments, and specifically relates to a method for re-calibrating non-dispersive infrared (NDIR) gas sensors whose outputs have drifted over time and no longer correctly reflect their measurement accuracy.

BACKGROUND OF THE INVENTION

Output stability or drift over time leading to measurement inaccuracies has long been a major deficiency for gas sensors irrespective of what technology or methodology is used for their conception or realization. Output software correction may alleviate the problem somewhat but it is in many instances inaccurate and not even always applicable. It has long been the objective of many researchers in this field to overcome this problem fundamentally and for good. Recently the present inventor in U.S. application Ser. No. 12/859,749 advanced the teaching of an Absorption Biased NDIR Gas Sensing Methodology which is capable of eliminating substantially all NDIR gas sensor output drifts over time without the need for re-calibration (Wong, filed 19-AUG-2010). As it turns out, the solution to solving this output drift problem for gas sensors actually lies deeper than the availability of superior NDIR gas sensor types even though they can indeed be designed to be capable of maintaining measurement accuracy over time. The fact of the matter is that people have experienced gas sensor output instability for such a long time in the past that when output stable sensors really come along nobody would believe it. Until such time that stable gas sensors become widely available and users begin to consider their performance as trustworthy and truly believable, the real need today must be viewed at a completely different perspective and that is to be able to come up with a fast, inexpensive and simple methodology that can easily check the accuracy of gas sensors and more importantly, just as easy and simple, hence inexpensive, to re-calibrate them when they are found to be inaccurate.

It is therefore the primary objective of the present invention for the present author to advance a novel methodology to simply and easily re-calibrate an NDIR gas sensor.

SUMMARY OF THE INVENTION

The present invention is generally directed to a method for recalibrating a dual-beam NDIR gas sensor by using a calibration curve that is based upon a combination of a physics measurement component of the NDIR gas sensor and a sensor measurement component of the NDIR gas sensor to calculate a first concentration of sample gas, then using a secondary gas standard to determine a second gas concentration of the sample gas, and then recalibrating the NDIR gas sensor by using the second gas concentration and a reversed calibration curve algorithm which adjusts the sensor measurement component to correct for any difference between the first concentration and the second gas concentration when the difference between the two exceeds a preselected threshold.

In a separate group of aspects of the present invention, the calibration curve (which expresses the concentration of the sample gas as an nth order, e.g., a third order polynomial of G) is based upon a gamma ratio ("G") that has been normalized by the gamma ratio when no sample gas is present in the sample chamber ("$G_0$"), G being a ratio of a signal channel output ("$V_S$") of the NDIR gas sensor divided by a reference channel output ("$V_R$") of the NDIR gas sensor. The concentration ("P") of sample gas in the NDIR gas sensor is calculated through use of the calibration curve by a gas detection equation of $P=F(x)=F(y/G_0)$, where x is a normalized ratio of $V_S/V_R$ and y is G. The reversed calibration curve algorithm, which is a non-linear equation, is $P=F(x)=F(y/G_{0N})$, where $G_{0N}=y_1/x_2$, $y_1=G$ for the NDIR gas sensor, $x_2=F^{-1}(P_2)$ and $P_2$ is the second gas concentration of the sample gas.

In another separate group of aspects of the present invention, the secondary gas standard (which can be a second NDIR gas sensor) is calibrated within a preselected time period prior to determining the second gas concentration and both the first concentration and the second concentration detect substantially the same concentration within a pre-selected space (e.g., a still space of less than 1,000 cubic feet). The second concentration can be transmitted to the NDIR gas sensor being recalibrated which receives the transmission and calculates gas concentration through electronics which use its calibration curve and recalibrate the NDIR gas sensor and then provide indication of recalibration.

Accordingly, it is a primary object of the present invention to provide an improved methodology for re-calibrating NDIR gas sensors whose outputs have drifted over time and no longer correctly reflect their measurement accuracy.

This and further objects and advantages will be apparent to those skilled in the art in connection with the drawings and the detailed description of the invention set forth below.

DETAILED DESCRIPTION OF THE INVENTION

The present invention complements the teaching of advancing a methodology for NDIR gas sensors capable of significantly reducing output drifts over time disclosed in U.S. Ser. No. 12/859,749, which is specifically incorporated herein by reference. It is important to point out the fact that such a methodology only applies to NDIR gas sensors and not to other technology types of gas sensors. It is therefore appropriate to begin the detailed description of the current invention by referencing the conventional and ever so popular dual-beam methodology for NDIR gas sensors. For purposes of illustration, the dual-beam methodology discussed herein is for the implementation of an NDIR $CO_2$ gas sensor. This methodology nevertheless also applies equally well to the detection of other gases having significant infrared absorption bands in the electromagnetic spectrum.

Figure 1:
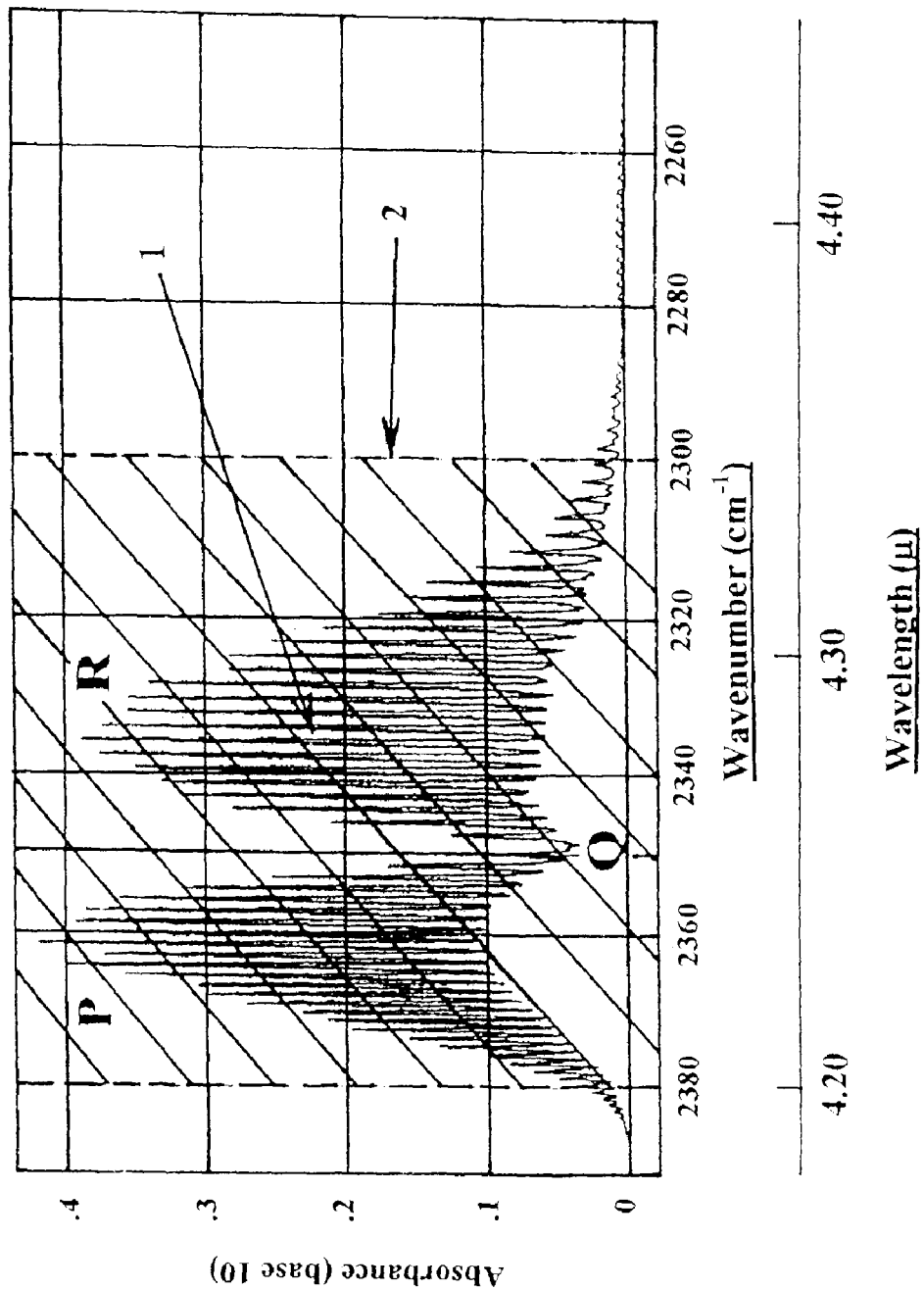
FIG. 1 depicts the 4.26μ infrared absorption bands of $CO_2$ expressed in absorbance units and a narrow band pass spectral filter with a Center Wavelength (CWL) at 4.26μ and a Full Width Half Maximum (FWHM) value of 0.14μ used optimally to detect this gas.

FIG. 1 shows the infrared absorption band 1 of $CO_2$ at 4.259μ showing respectively the P, Q and R branches. FIG. 1 also shows the spectral characteristics of a narrow band pass filter 2 with Center Wavelength (CWL)=4.26μ and Full Width Half Maximum (FWHM)=0.14μ (shaded area) used in the design for the signal channel of a conventional NDIR $CO_2$ sensor. To complete this design, another spectral narrow band pass filter with CWL=3.91μ and FWHM=0.10μ (not shown in FIG. 1), which does not overlap the 4.26μ absorption band of $CO_2$, is used for the reference channel. As can be seen from FIG. 1, the 4.26μ absorption band of $CO_2$ is actually comprised of a number of rotation-vibrational narrow absorption lines constituting the P and the R branches. Those radiation emanating from the infrared source whose spectral positions (wavelengths) coincide with the narrow absorption lines of the P and R branches will be absorbed by the $CO_2$ gas as the radiation traverses the sample chamber containing same.

The technical foundation of NDIR gas sensors is based upon the law of absorption known as the Beer-Lambert Law:

$$I/I_o = \mathrm{Exp}(-kCL) \quad (1)$$

Where
  $I_o$=Initial radiation beam intensity
  I=Beam intensity after traversing the gas to be detected
  k=Absorption coefficient=AC/(0.434×C×L)
  AC=Absorbance (Ordinate of FIG. 1)
  C=Gas concentration
  L=Sample path length defined typically by the effective sample chamber length of the sensor and
  $I/I_o$=Transmission=1−Absorption=Exp(−AC/0.434)

One can see from Equation (1) above that the absorption of a beam of radiation traversing a sample of gas whose concentration level is to be determined is proportional to the absorption coefficient k of the gas in question, the gas concentration C and the path length L as defined by the sample chamber length for the sensor. Based upon the spectral characteristics of a typical infrared absorption band, e.g. see FIG. 1 for the $CO_2$ gas, the absorption of the intensity of a radiation beam by the gas could rarely be complete (i.e. 100% absorbed) unless the gas concentration approaches 100% and is also at a very high pressure (e.g. hundreds of bars) so that the individual narrow absorption lines of the branches coalesce together to form a bottomed-out spectral band.

Figure 2:
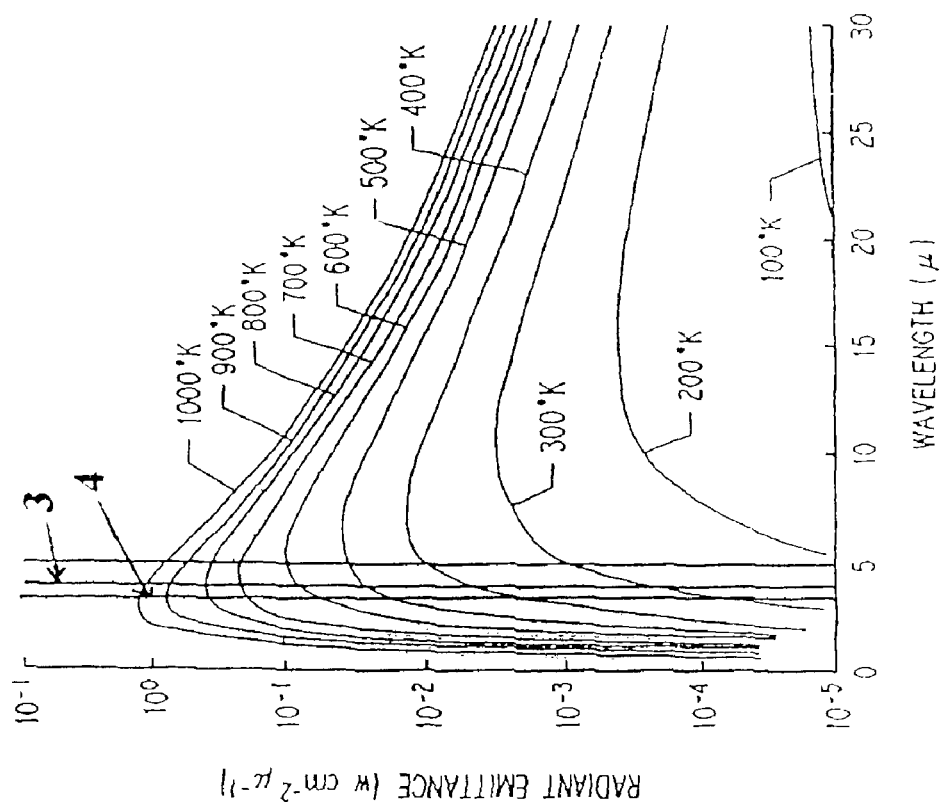
FIG. 2 depicts the conventional signal and reference narrow band pass filters at 4.26μ and 3.91μ respectively used in the design of a dual-beam NDIR $CO_2$ sensor superimposed on the spectral radiant excitance curves of a blackbody source at temperatures between 100° K and 1,000° K.

In the design for NDIR gas sensors, almost all infrared sources without exception are graybodies, so-called because the emissivity of these sources is always less than unity. However, Planck's radiation law comprising a family of spectral radiation curves for sources of diverse temperatures represents equally well both graybody and blackbody (emissivity=1) sources. FIG. 2 depicts the spectral radiant excitance curves of a blackbody source at temperatures between 100° K and 1,000° K. Superimposed on this curve are the spectral locations for the signal, 3, and reference, 4, narrow band pass spectral filters at 4.26μ and 3.91μ respectively.

One can see from FIG. 2 that if the temperature of the source changes, thereby shifting the Planck's spectral radiation excitance curve, the relative magnitudes of the radiation traversing the two filters at their respective spectral locations changes and so also the ratio of their respective detector outputs. This is precisely the reason why the outputs of all NDIR gas sensors today that utilize this so-called "Double Beam" methodology will drift over time as the infrared source ages resulting in a change of its spectral output intensities at the signal and reference filter wavelengths. Thus, the sensor output expressed as the ratio of the signal channel detector output over the same for the reference channel can never be held constant over time. Against the calibration curve for the sensor, the change of this ratio value is equivalent to a change or drift in the sensor output in the course of time.

Using a spectral location where there is no infrared absorption by the gas of interest for establishing a reference channel cannot prevent the output of the so-designed NDIR gas sensor from drifting over time. In order to design an NDIR gas sensor whose output remains drift-free over the course of time, one must make sure there is no spectral content discrepancies delivered at any time to both the reference and the signal channel detectors. Only in this way will the ratio of the signal detector output over the reference detector output remain almost completely invariant even as the infrared source ages over time or as the temperature of the environ surrounding the sensor changes unpredictably over the course of time.

The inventor's earlier teaching achieves this feat, namely no spectral content discrepancies will be delivered at any time to both the reference and the signal channel detectors, by using the same spectral narrow band pass filter for wavelength selection for both the signal and reference channels. An absorption bias is additionally applied to the signal channel by making the sample chamber path length associated with it longer than that associated with the reference channel.

Figure 3:
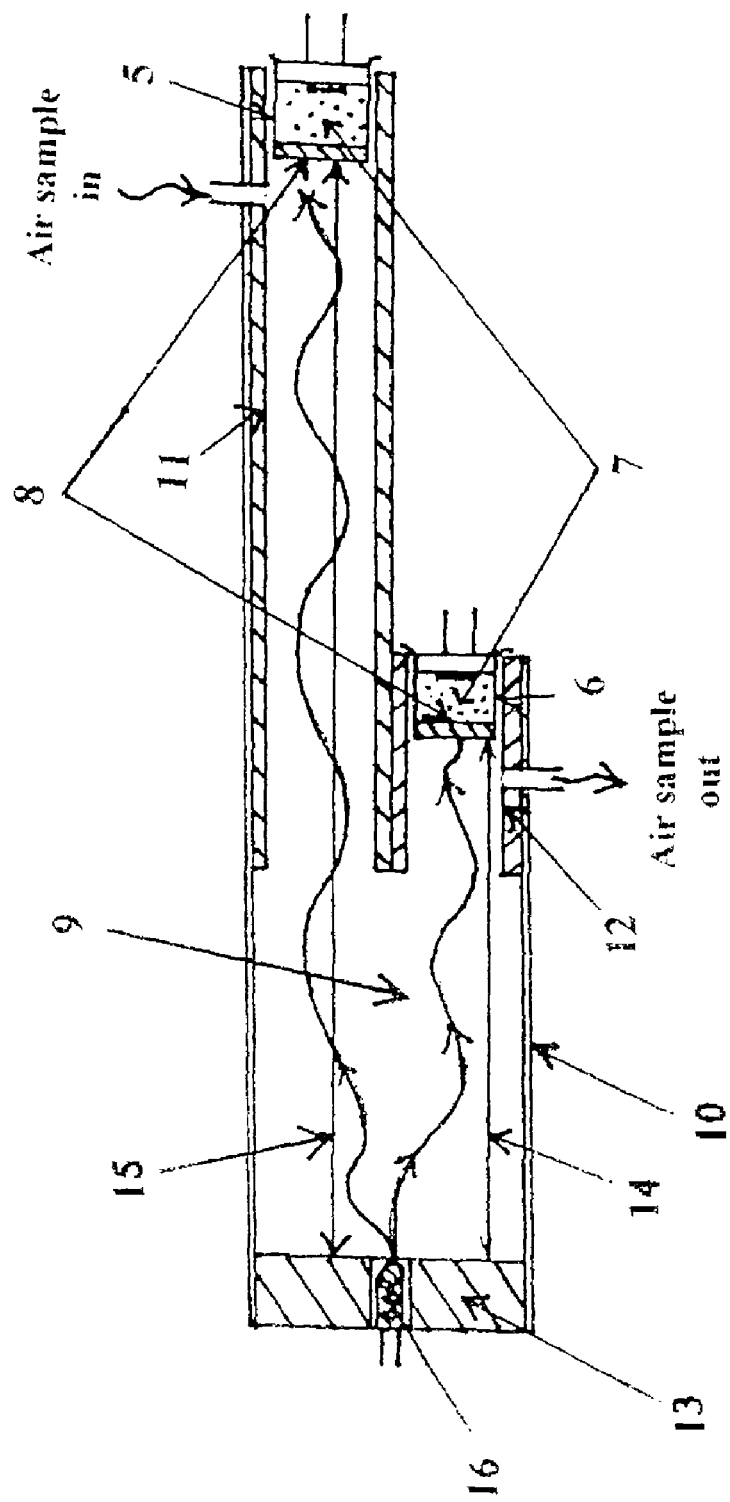
FIG. 3 depicts the schematic components layout for the Absorption Biased (AB) NDIR gas sensing methodology.

FIG. 3 depicts the optical component layout for the earlier advanced Absorption Biased methodology for NDIR gas sensors. As shown in FIG. 3, both the signal channel detector 5 and the reference detector channel 6 are entrapped with 100% Nitrogen 7 and have the same narrow band pass spectral filter 8 which is used to detect the gas of interest in the sample chamber 9. In our example, the filter designed to be used for the detection of $CO_2$ gas would have a Center Wavelength (CWL)=4.26μ and a Full Width Half Maximum (FWHM)=0.14μ. Noting that the detectivity of infrared detectors is a function of their operating temperature, both detectors 5 and 6 in our design are thermally connected to the entire sensor body 10 through their respective waveguides 11 and 12 and consequently they always share the same thermal platform with each other and have approximately the same operating temperature. In other words, the entire sensor body 10 which is in essence a composite of aluminum parts comprising the infrared source mount 13, sample chamber 9 and the waveguides 11 and 12 respectively for the signal and reference channels, provides an excellent common thermal platform for detectors 5 and 6.

As shown in FIG. 3, the sample chamber pathlength $L_R$, 14, associated with the reference channel is approximately one-half of the sample chamber pathlength $L_S$, 15, associated with the signal channel. A common infrared source 16 is used to illuminate both the signal and the reference channels. The output of the detector 5 for the signal channel is always less than that of the detector 6 for the reference channel irrespective of whether or not there is any amount of the gas of interest in the sample chamber 9. The respective detector outputs can be determined with the use of Equation (1) above for the particular gas of interest and the designed characteristics of the narrow band pass filter 8 together with the physical dimensions for $L_R$ 14 and $L_S$ 15. In other words as pointed out earlier the technical foundation of NDIR gas sensors is very Physics oriented and is based strictly upon the law of absorption known as the Beer-Lambert Law as shown in Equation (1).

Figure 4:
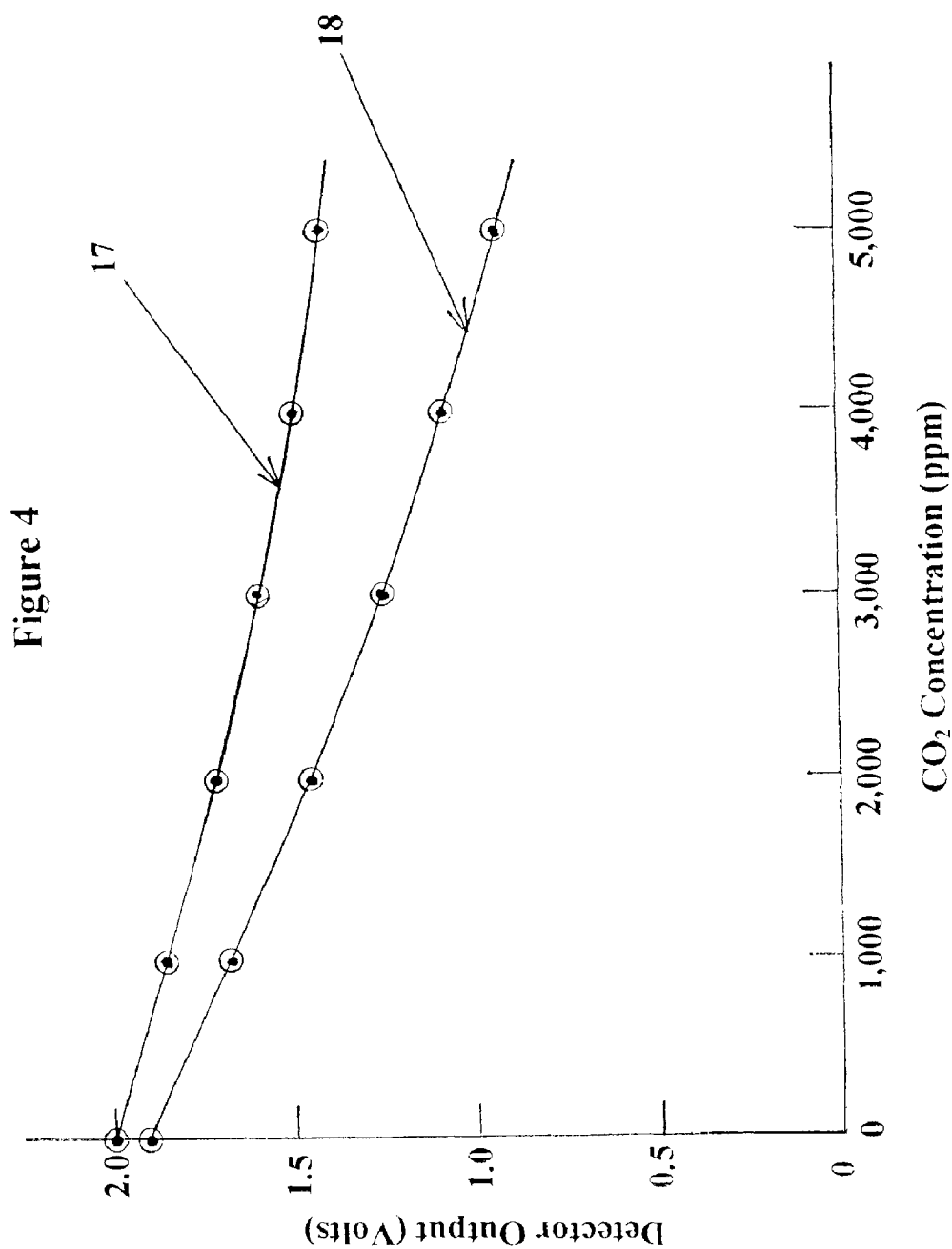
FIG. 4 depicts the detector outputs for the signal and reference channels as a function of CO2 concentration in the sample chamber for the Absorption Biased (AB) NDIR gas sensing methodology.

FIG. 4 shows graph 17 depicting the output of reference channel detector 6 as a function of $CO_2$ concentration in sample chamber 9. Graph 18 of FIG. 4 shows output of signal channel detector 5 as a function of $CO_2$ concentration in sample chamber 9. Notice that detector output of signal channel detector 5 is invariably less than that of reference channel detector 6 when there is $CO_2$ gas present in sample chamber 9. The reason is that sample path length $L_R$ 14 of the reference channel is shorter than the signal channel sample pathlength $L_S$ 15 (see FIG. 3). Therefore, whenever there is $CO_2$ gas present in sample chamber 9, signal channel detector 5 will experience more absorption by $CO_2$ gas than the corresponding reference channel detector due to its longer associated pathlength $L_S$ 15.

Figure 5:
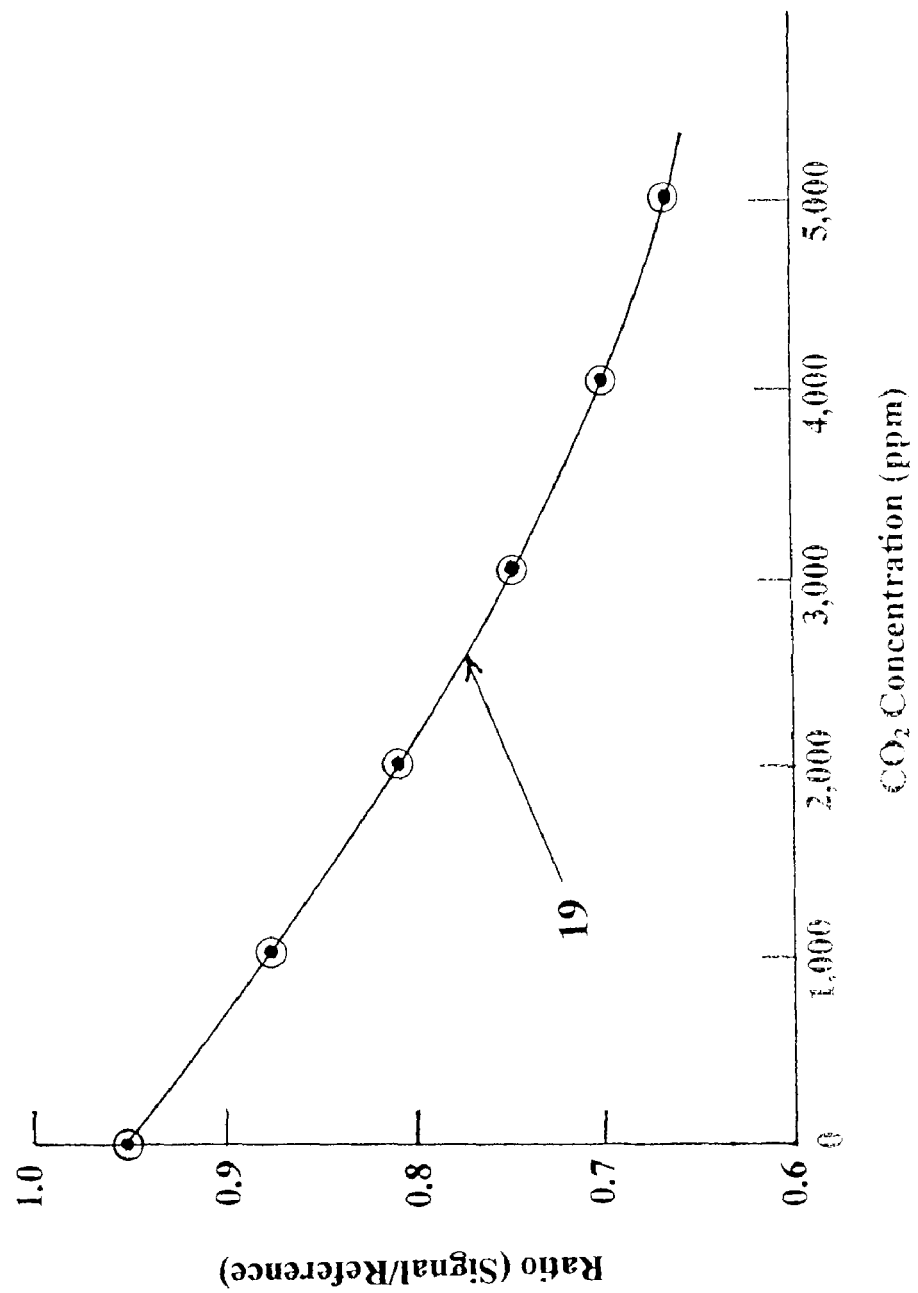
FIG. 5 depicts the ratio of signal output/reference output as a function of $CO_2$ concentration in the sample chamber for the Absorption Biased (AB) NDIR gas sensing methodology.

FIG. 5 shows graph 19 depicting the ratio of signal channel output over reference channel output as a function of $CO_2$ concentration in sample chamber 9.

Figure 6:
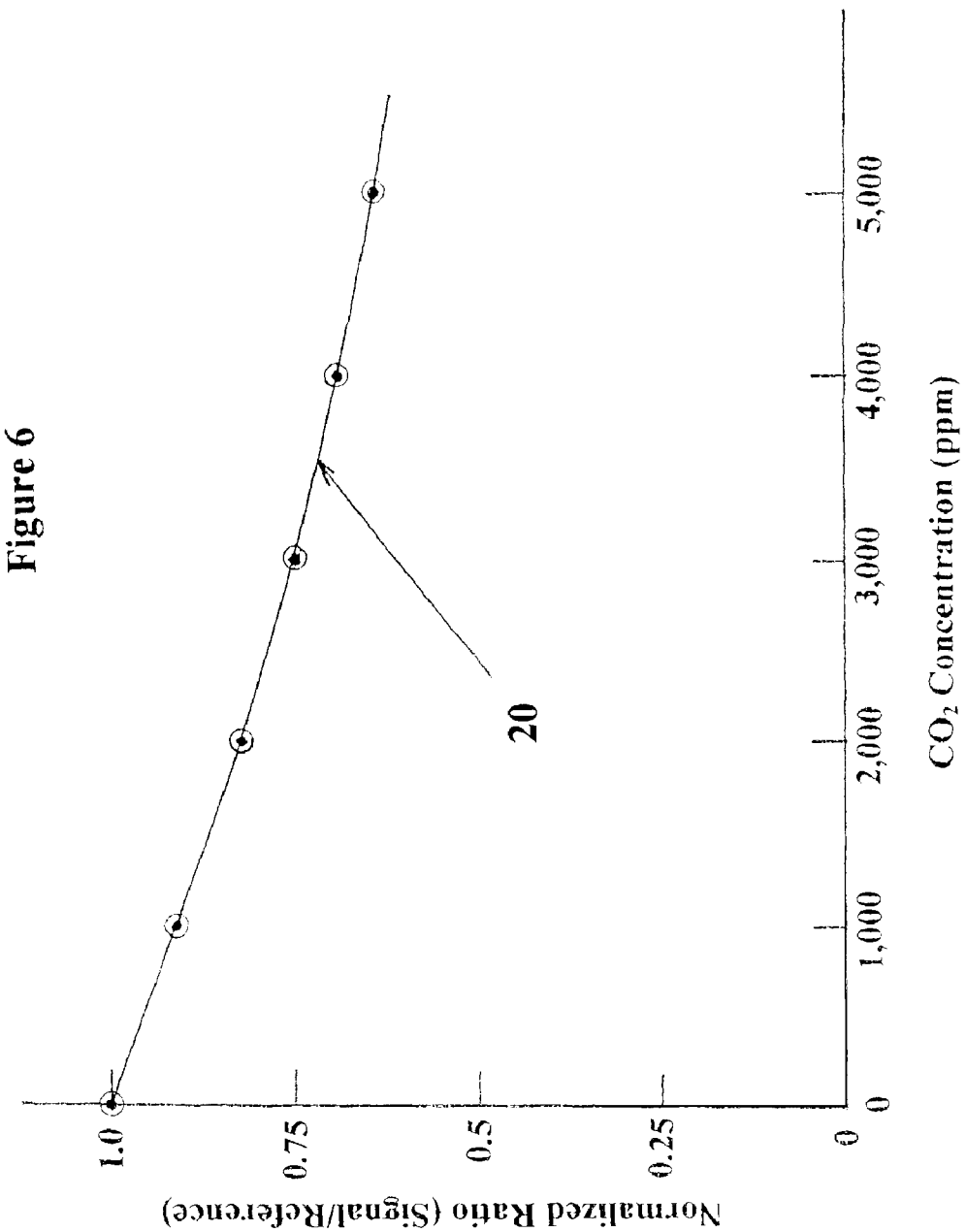
FIG. 6 depicts the normalized ratio of signal output/reference output as a function of $CO_2$ concentration in the sample chamber for the Absorption Biased (AB) NDIR gas sensing methodology.

In other words, the values of graph 19 shown in FIG. 5 are obtained by dividing the values of graph 18 by those of graph 17 depicted in FIG. 4. In conventional NDIR dual-beam methodology, the ratio value of the signal channel output over the reference channel output is used to process the different gas concentrations present in the sample chamber. The rationale behind this practice is to make sure that any common changes in both signal and reference channel components over time (short or long term) can be cancelled out without affecting sensor measurement accuracy. Such common changes might be dimming of the infrared source over time, dirtying of sensor optical components such as windows and the sample chamber and any responsivity value changes for the two similar infrared detectors, which are known to track one another in aging characteristics. One additional and important step in NDIR dual-beam methodology is to normalize this ratio with that value when there is no $CO_2$ gas present in the sample chamber as depicted in FIG. 6. As can be seen in FIG. 6, the normalized ratio as represented by graph 20 always starts out with a value of unity when there is zero $CO_2$ concentration in the sample chamber 9. Graph 20 is in essence the calibration curve for the NDIR gas sensor implemented with the earlier Absorption Biased (AB) methodology advanced earlier by the present inventor.

The present invention recognizes the importance of the ratio value, designated as "Gamma", obtained by dividing signal channel output over that of the reference channel output when there is no $CO_2$ gas present in the sample chamber. By normalizing the dual-beam ratio outputs for the signal and reference channels with Gamma to obtain the calibration curve for the NDIR gas sensor as shown in FIG. 6, one is able to separate the invariant Physics constituent of the NDIR gas sensing principle from the other inevitably changing component parts constituent of the sensor over time. In other words, any changes in the calibration curve for an appropriately designed and implemented NDIR gas sensor will only be reflected in the changing value of Gamma over time. It will not be reflected in the Physics measurement principle of such an NDIR gas sensor, which is supposed to always remain invariant. The output of the infrared source for any NDIR gas sensor, if designed to be received spectrally different over time by the signal and reference channel detectors, would destroy the invariance of the Physics measurement principle for the sensor. As it turns out, the present inventor's earlier teaching in advancing the Absorption Biased methodology for NDIR gas sensors is an appropriate design approach that will not permit spectral content discrepancies to be delivered at any time to both the signal and reference channel detectors. This is because both the signal and the reference channel detectors are provided with exactly the same spectral filter for the detection of a particular gas, in the present example $CO_2$. Also, by knowing that the performance characteristics of infrared detectors are a strong function of their operating temperature and also that their spectral aging characteristics track one another if they are of the same kind, designing the signal and reference detectors to share the same thermal platform further preserves the invariance of the Physics measurement principle for the sensor over time.

The present invention complements the earlier disclosed Absorption Biased methodology for designing NDIR gas sensors, in an especially preferred embodiment, by first transforming graph 20 of FIG. 6 into a curve that expresses the amount of $CO_2$ gas present in the sample chamber, P(ppm), as an nth order polynomial of parameter R where R is the normalized ratio of the signal channel detector output over the reference channel detector output when there is $CO_2$ present in the sample chamber. For a third order polynomial, which is plenty accurate for most applications, this calibration curve transformation can be quantitatively expressed in terms of P(ppm), R and Gamma as follows:

$$P(ppm) = A_0 + A_1 \times R + A_2 \times R^2 + A_3 \times R^3 \quad (2)$$

$$\text{Gamma} = V_{S0} N_{R0} (\text{zero gas in sample chamber}) \quad (3)$$

$$R = (V_S N_R) / \text{Gamma} \quad (4)$$

where $V_S$ and $V_R$ are respectively the signal and reference channel detector outputs when there is $CO_2$ gas in the sample chamber. Note that in this transformation of the calibration curve for the sensor, P (ppm) and Gamma of Equations (2) and (3) above represent respectively the invariant Physics principle portion and the inevitably variant components portion of the methodology. But since parameter R is a function of Gamma (see Equation [4]), when there is a change in the value for Gamma over time and not corrected, R will be affected and the calibration curve for the sensor will change accordingly leading to sensor output drifts. However, if for whatever reason the change in Gamma over time is known, the value of R can be corrected and restored to its earlier value thereby preserving the original calibration curve for the sensor as represented by Equation (2). Under this circumstance, no output drifts will be detected from the sensor and it will stay accurate over time.

The present invention provides an important additional step to the earlier disclosed Absorption Biased methodology for designing NDIR gas sensors in order to achieve the objective of attaining a simple, easy and inexpensive re-calibration methodology for such sensors. This is first done by reversing the expression of P (ppm) as a third order polynomial of R as depicted in Equation (2) above into one where R is expressed as a third order polynomial of P (ppm) without changing the value of Gamma as shown below:

$$R = B_0 + B_1 \times P + B_2 \times P^2 + B_3 \times P^3; \text{ Gamma unchanged} \quad (5)$$

All sensors manufactured with the presently invented re-calibration methodology, in an especially preferred embodiment, will carry both polynomials, namely Equation (2) and Equation (5), in their Central Processing Unit (CPU) memory.

Assume now that an NDIR gas sensor, in the current example $CO_2$, is calibrated with a calibration curve characterized by a third order polynomial with coefficients ($A_0, A_1, A_2, A_3$) and Gamma=$G_0$. As time goes by it is recognized that the sensor no longer accurately detects $CO_2$ and we wish to re-calibrate this sensor to its original accuracy or calibration curve. To do this, one has to first prepare a secondary gas (in the current example $CO_2$) standard, preferably in the form of a similar NDIR gas sensor which accurately detects and measures the $CO_2$ concentration. This secondary gas standard and the sensor to be re-calibrated are then put in the same still ambience (no wind or air movement within the space) preferably within a space volume of less than 1,000 cu. ft. The objective here is to make sure that both the secondary gas standard and the sensor to be re-calibrated sense or detect the same gas concentration value within this still space. The gas concentration value in the space as measured by the secondary gas standard is now, in an especially preferred embodiment, transmitted (via wired or wireless communication) to the sensor to be re-calibrated. Upon receipt of this information, the sensor to be re-calibrated compares this received $CO_2$ concentration value with the one that it meanwhile also measures by determining the value for R and using the stored calibration curve (Equation [2]) and the Gamma value of $G_0$. If the gas concentration values are found out to be within the expected accuracy limit (say +/−25 ppm), a signal will be sent back to the secondary gas standard conveying the message that its measurement is good and the unit remains accurately calibrated. However, if the compared values lie outside the expected accuracy limit, then the unit needs re-calibration and will attempt to re-calibrate itself automatically as outlined below.

Using the received gas concentration value, it calculates the corresponding R value using the stored reverse calibration curve (Equation [5]), namely ($B_1$, $B_2$, $B_3$, $B_4$). Using this newly calculated R value, the stored Gamma value of $G_0$ and the R value from its own gas measurement earlier that reports the inaccurate gas reading, a new Gamma, $G_N$, can now be determined. By replacing the old Gamma=$G_0$ with the newly determined $G_N$ but retaining the original calibration curve (Equation [2]), namely ($A_0$, $A_1$, $A_2$, $A_3$), the sensor has just automatically re-calibrated itself. This process of recalibration can be repeated indefinitely with the new $G_N$ now functioning as the prior $G_0$ during the next recalibration.

Several factors are paramount and very close attention must be paid to such factors in order to make sure that the currently invented re-calibration methodology works properly and stays valid.

The first and most important factor is to make sure that the secondary gas standard (such as a NDIR Absorption Biased gas sensor) used in the re-calibration methodology is accurate. Such a secondary gas standard should be and could be frequently re-calibrated with a primary gas standard supplied by calibrated gas sources in the form of certified gas cylinders. Frequently re-calibrating the secondary gas standard with a primary one prior to its use can be easily achieved using the same re-calibrating methodology advanced in the current invention. But since the secondary gas standard is designed according to the NDIR Absorption Biased methodology, it should remain stable most of the time and its re-calibration routine using the primary standard should be no more than a simple and easy accuracy check routine.

The second important factor is to make sure that the gas concentration level sensed or detected by both the secondary gas standard and the sensor to be re-calibrated are substantially the same, which means that they are exactly the same within specified measurement accuracy. In order for this to happen, the air space wherein the two sensors reside for the re-calibration routine must be still and have no air movement of any kind within it during the re-calibration time span.

A final important factor is that electrical communication (wired or wireless) between the secondary gas standard and the sensor to be re-calibrated must be robust and free from any interferences or disturbances. The sensor to be re-calibrated must receive a valid and accurate gas concentration level information of the relevant space from the secondary gas standard before it can properly re-calibrate itself. Once the sensor receives this information, by means of wireless or wired connection, it can institute re-calibration of itself. This re-calibration can be automatic or only proceed if the difference between the gas concentration measured by the sensor and the information received from the secondary gas standard (e.g., another NDIR gas sensor) exceeds a preselected threshold (e.g., the accuracy by which the secondary gas standard can detect the gas concentration of interest). Once re-calibration has been instituted, the sensor can indicate whether any re-calibration has occurred and the amount of such re-calibration. Information about re-calibration can be transmitted by wired or wireless communication to a control point (e.g., a computer monitoring multiple sensors), stored in memory (where it may be obtained by later interrogation) or displayed visually, depending upon designer choice and any specialized needs of a user of the sensor.

The most significant advantage of the currently invented re-calibration methodology for NDIR gas sensors is the fact that it can re-calibrate a sensor in a particular space or location without the need to use any certified gas standards such as a 100% dry nitrogen bottle or a 1,000 ppm $CO_2$ balanced with dry nitrogen gas cylinder. Instead, it simply uses the gas concentration level of the space or location wherein the sensor to be re-calibrated resides. In addition to tremendous labor savings because of the ease and simplicity of the currently invented re-calibration methodology, this also translates into very significant material and hardware savings when commissioning buildings or re-calibrating installed gas sensors in commercial buildings.

Accordingly, the present invention advances a novel re-calibration methodology for NDIR gas sensors which is both simple and easy that can be very inexpensively carried out. The current invention is achieved via extending the earlier disclosed NDIR Absorption Biased gas sensing methodology into two distinct domains. One domain is identified to involve only the Physics measurement constituent of the methodology and therefore should always remain invariant towards the sensor's output performance. The other domain is identified to be the sensor components constituent and is responsible for the sensor's variant output behavior over time. The concept of Gamma, which is the ratio of the signal detector output over the reference detector output when there is no gas present in the sample chamber, has been introduced to represent the variant components domain for the sensor re-calibration methodology. By so doing, the two identified constituent methodology domains can be separated. With the use of a reversed calibration curve algorithm linking gas concentration with the Gamma-normalized ratio of the signal detector output over the reference detector output, any output drifts exhibited by the sensor over time can be easily rectified by simply updating the value of Gamma with the use of a secondary gas standard effectively re-calibrating the sensor itself.

While the invention has been described herein with reference to certain examples, those examples have been presented for illustration and explanation only, and not to limit the scope of the invention. Additional modifications and examples thereof will be obvious to those skilled in the art having the benefit of this detailed description. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A method useful with a dual-beam non-dispersive infrared ("NDIR") gas sensor having a sample chamber used to detect a sample gas, comprising:
    using a calibration curve of the NDIR gas sensor to calculate a first concentration of the sample gas in the sample chamber of the NDIR gas sensor;
    using a secondary gas standard to determine a second gas concentration of the sample gas; and
    recalibrating the NDIR gas sensor to create a recalibrated gas sensor by using the second gas concentration and a reversed calibration curve algorithm which adjusts the sensor measurement component to correct for a difference between the first concentration and the second gas concentration when the difference exceeds a preselected threshold;
    wherein the NDIR gas sensor has no moving parts for effecting the interposition of a plurality of spectral filters or an absorbing cell or a non-absorbing cell to create both a signal channel and a reference channel; and
    wherein the calibration curve is based upon a combination of a physics measurement component of the NDIR gas sensor and a sensor measurement component of the NDIR gas sensor.

2. The method of claim 1, wherein the reversed calibration curve algorithm is a non-linear equation.

3. The method of claim 2, wherein the calibration curve is based upon a gamma ratio ("G") that has been normalized by the gamma ratio when no sample gas is present in the sample chamber ("$G_0$"), G being a ratio of a signal channel output ("$V_S$") of the NDIR gas sensor divided by a reference channel output ("$V_R$") of the NDIR gas sensor.

4. The method of claim 3, wherein the concentration ("P") of the sample gas in the sample chamber of the NDIR gas sensor is calculated through use of the calibration curve by a gas detection equation of $$P=F(x)=F(y/G_0) \text{ where:}$$

x is a normalized ratio of $V_S/V_R$; and
y is G.

5. The method of claim 4, wherein the secondary gas standard is comprised of a second NDIR gas sensor.

6. The method of claim 5, wherein the reversed calibration curve algorithm is:

$$P=F(x)=F(y/G_{0N}) \text{ where:}$$

$G_{0N}=y_1/x_2$ where:
    $y_1$=G for the NDIR gas sensor; and
    $x_2=F^{-1}(P_2)$ where $P_2$ is the correct gas concentration of the sample gas.

7. The method of claim 6, wherein the calibration curve expresses the concentration of the sample gas as an nth order polynomial of G.

8. The method of claim 7, wherein the nth order polynomial is a third order polynomial.

9. The method of claim 1, wherein the secondary gas standard is comprised of a second NDIR gas sensor.

10. The method of claim 9, wherein the secondary gas standard is calibrated within a preselected time period prior to determining the second gas concentration.

11. The method of claim 1, wherein the first concentration and the second concentration detect substantially the same concentration within a pre-selected space.

12. The method of claim 11, wherein the pre-selected space is a still space.

13. The method of claim 12, wherein the pre-selected space is less than 1,000 cubic feet.

14. The method of claim 1, wherein the second concentration is transmitted to the NDIR gas sensor.

15. The method of claim 14, wherein the preselected threshold is zero.

16. The method of claim 1, wherein the NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel path length.

17. The method of claim 1, wherein the sample gas is not comprised of carbon dioxide.

18. A method useful with a dual-beam non-dispersive infrared ("NDIR") gas sensor having a sample chamber used to detect a sample gas, comprising:
    calculating a gas concentration ("P") of the sample gas detected by the NDIR gas sensor through use of a calibration curve for the NDIR gas sensor, said calibration curve being obtained from a gamma ratio ("G") that has been normalized by the gamma ratio when no sample gas is present in the sample chamber ("$G_0$"), G being the ratio of a signal channel output ("$V_S$") of the NDIR gas sensor divided by a reference channel output ("$V_R$") of the NDIR gas sensor; and
    recalibrating the NDIR gas sensor by comparing P to a second gas concentration of the sample gas determined by a master NDIR gas sensor and adjusting $G_0$ based upon a reversed calibration curve algorithm that is a non-linear equation if a difference between P and the second gas concentration exceeds a preselected threshold.

19. The method of claim 18, wherein the NDIR gas sensor has no moving parts for effecting the interposition of spectral filters or an absorbing cell or a non-absorbing cell to create both the signal channel and the reference channel.

20. The method of claim 19, wherein the NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel path length.

21. In a dual-beam non-dispersive infrared ("NDIR") gas sensor having a sample chamber used to detect a sample gas through use of electronics that receives a signal channel output ("VS") and a reference channel output ("$V_R$"), the improvement, comprising:
    electronics for calculating a gas concentration ("P") of the sample gas detected by the NDIR gas sensor through use of a calibration curve for the NDIR gas sensor, said calibration curve being obtained from a gamma ratio ("G") that has been normalized by the gamma ratio when no sample gas is present in the sample chamber ("$G_0$"), G being the ratio of a signal channel output ("$V_S$") of the NDIR gas sensor divided by a reference channel output ("$V_R$") of the NDIR gas sensor; and
    recalibration electronics for recalibrating the NDIR gas sensor by comparing P to a second gas concentration of the sample gas determined by a secondary gas standard and adjusting $G_0$ based upon a reversed calibration curve algorithm that is a non-linear equation if a difference between P and the second gas concentration exceeds a preselected threshold;

wherein the NDIR gas sensor has no moving parts for effecting the interposition of a plurality of spectral filters or an absorbing cell or a non-absorbing cell to create both the signal channel and the reference channel.

22. The dual-beam NDIR gas sensor of claim 21, further comprising:
   means for receiving transmission of the second gas concentration.

23. The NDIR gas sensor of claim 21, wherein the NDIR gas sensor uses an identical spectral narrow band pass filter for wavelength selection for both a signal channel having a signal channel pathlength and a reference channel having a reference channel pathlength and an absorption bias is applied to the signal channel by making the signal channel path length longer than the reference channel pathlength.

24. The NDIR gas sensor of claim 23, wherein the NDIR gas sensor does not contain a standard cell containing the sample gas.

25. The NDIR gas sensor of claim 24, wherein the sample gas is not comprised of carbon dioxide.

* * * * *